(12) United States Patent
Kamee et al.

(10) Patent No.: US 10,327,622 B2
(45) Date of Patent: Jun. 25, 2019

(54) ENDOSCOPE

(71) Applicant: OLYMPUS CORPORATION, Tokyo (JP)

(72) Inventors: Hiroyuki Kamee, Koganei (JP); Satoshi Ohara, Hachioji (JP); Motoki Tabata, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 196 days.

(21) Appl. No.: 15/375,835

(22) Filed: Dec. 12, 2016

(65) Prior Publication Data

US 2017/0086648 A1 Mar. 30, 2017

Related U.S. Application Data

(63) Continuation of application No. PCT/JP2015/064613, filed on May 21, 2015.

(30) Foreign Application Priority Data

Jun. 13, 2014 (JP) .................................. 2014-122622

(51) Int. Cl.
| | |
|---|---|
| *A61B 1/05* | (2006.01) |
| *A61B 1/06* | (2006.01) |
| *A61B 1/273* | (2006.01) |
| *A61B 1/00* | (2006.01) |
| *A61B 5/00* | (2006.01) |
| *A61K 49/00* | (2006.01) |

(Continued)

(52) U.S. Cl.
CPC ............ *A61B 1/00009* (2013.01); *A61B 1/05* (2013.01); *A61B 1/063* (2013.01); *A61B 1/0638* (2013.01); *A61B 1/0646* (2013.01); *A61B 1/0676* (2013.01); *A61B 1/273* (2013.01); *A61B 5/0071* (2013.01); *A61K 49/006* (2013.01); *G02B 23/2476* (2013.01); *H04N 5/2256* (2013.01); *H04N 5/23245* (2013.01); *H04N 2005/2255* (2013.01)

(58) Field of Classification Search
CPC ........... A61B 5/00; A61B 5/04; A61B 5/0084; A61B 5/04001; A61B 5/4064; A61B 5/0071; A61B 5/4519
USPC ......................................................... 600/476
See application file for complete search history.

(56) References Cited

U.S. PATENT DOCUMENTS

| | | | | |
|---|---|---|---|---|
| 2004/0143190 A1* | 7/2004 | Schnitzer | ............. | A61B 5/0084 600/476 |
| 2015/0086955 A1* | 3/2015 | Poniatowski | .......... | G09B 23/28 434/267 |

FOREIGN PATENT DOCUMENTS

| | | |
|---|---|---|
| JP | 2008-273900 A | 11/2008 |
| JP | 2012-143348 A | 8/2012 |
| JP | 2014-094175 A | 5/2014 |

OTHER PUBLICATIONS

International Search Report dated Aug. 25, 2015 issued in PCT/JP2015/064613.

(Continued)

*Primary Examiner* — Jon Eric C Morales
(74) *Attorney, Agent, or Firm* — Scully, Scott, Murphy & Presser, P.C.

(57) ABSTRACT

An endoscope includes an observation mode switch to switch observation modes. The observation modes include a dye valid observation mode allowed to acquire an image in which the dye is visually recognized well, and a dye invalid observation mode allowed to acquire an image in which the dye is substantially not visually recognized.

10 Claims, 8 Drawing Sheets

(51) Int. Cl.
    *H04N 5/225*    (2006.01)
    *H04N 5/232*    (2006.01)
    *G02B 23/24*    (2006.01)

(56) References Cited

OTHER PUBLICATIONS

Chinese Office Action dated Aug. 1, 2017 in Chinese Patent Application No. 201580031544.7.
Japanese Office Action dated Feb. 27, 2018 in Japanese Patent Application No. 2014-122622.
International Preliminary Report on Patentability and Written Opinion dated Dec. 22, 2016 received in International Application No. PCT/JP2015/064613.

* cited by examiner

ENDOSCOPE

CROSS REFERENCE TO RELATED APPLICATIONS

This application is a Continuation application of PCT Application No. PCT/JP2015/064613, filed May 21, 2015 and based upon and claiming the benefit of priority from Japanese Patent Application No. 2014-122622, filed Jun. 13, 2014, the entire contents of all of which are incorporated herein by reference.

BACKGROUND OF THE INVENTION

1. Field of the Invention

The present invention relates to an endoscope.

2. Description of the Related Art

At present, a "dye observation method" to disperse various dyes during an endoscopic inspection and observe their reactions and others are considered to be effective in early recognition of lesions, particularly cancer, determination of a lesion range, and assessment of the degree of invasion. There are various kinds of dyes that are characterized by, for example, being different from one another in principle and color. Dyes to be used differ depending on parts and lesions. However, living bodies principally show red-based colors, and a blue dye, which absorbs long-wavelength-side yellow and red components, is often used in order to form a contrast with the red-based colors.

Jpn. Pat. Appln. KOKAI Publication No. 2008-273900 discloses a such dye observation method. According to this literature, it is possible to easily recognize a boundary between a lesion part and a normal part by dispersing an indigo carmine aqueous solution having a density of 0.08 to 0.25 w/v % and an acetic acid aqueous solution having a density of 3.0 to 5.0 w/v % to an observation part at the same time or at an interval of a predetermined time during an endoscopic inspection.

BRIEF SUMMARY OF THE INVENTION

The present invention is directed to an endoscope to observe a subject in which a dye is dispersed. The dye is a material having a light absorbing wavelength region and a light transmission wavelength region in a visible light wavelength region. The endoscope includes an observation mode switch to switch observation modes. The observation modes includes a dye valid observation mode allowed to acquire an image in which the dye is visually recognized well, and a dye invalid observation mode allowed to acquire an image in which the dye is substantially not visually recognized.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of the present invention will be described with reference to the drawings.

[First Embodiment]

The present embodiment shows an endoscope capable of performing a "normal light observation". Here, the endoscope refers to an observation apparatus having an observation function at the distal end of an elongated insertion section to observe, image, and diagnose the inside of a narrow closed space. The normal light observation refers to an observation for image reproduction of an appearance of a subject when sunlight or an illumination showing a white light is applied thereto. An illumination to form an image of the normal light observation is referred to as a normal light illumination.

This endoscope is capable of two kinds of normal light observations with respect to a subject having the dye dispersed therein: a "dye valid observation" capable of acquiring a normal light observation image in which optical characteristics of a dye validly act on an illumination light, so that the dye is visually recognized well; and a "dye invalid observation" capable of acquiring a normal light observation image in which optical characteristics of a dye are substantially invalidated relative to an illumination light, so that the dye substantially behaves as a transparent liquid and the dye is therefore substantially not visually recognized.

Figure 1:
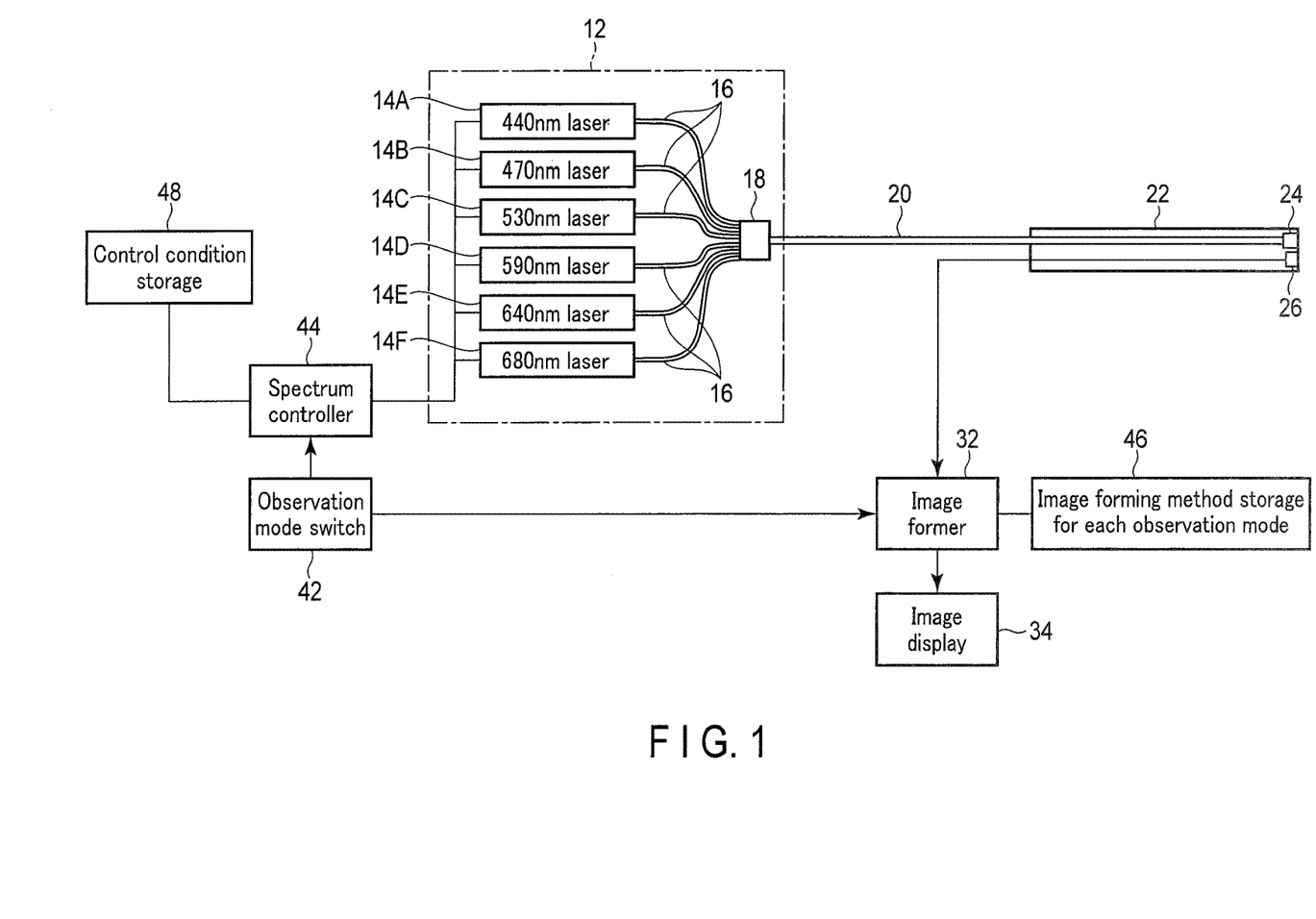
FIG. 1 shows a schematic constitution of an endoscope according to a first embodiment.

A schematic constitution of the endoscope according to the present embodiment is shown in FIG. 1. This endoscope comprises a light source section 12 that outputs a light to illuminate a subject, an optical fiber 20 that guides the light from the light source section 12, and a scope insertion section 22 that has a function to apply an illumination light to the subject and photograph the subject.

The optical fiber 20 may comprise a single-wire fiber, or a bundle fiber in which multiple fibers are bundled.

The scope insertion section 22 comprises, at its distal end, a light converting member 24 that converts a light guided by the optical fiber 20 into a light suited to the illumination of the subject, and an image sensor 26 that acquires an optical image of the subject and converts the optical image into an electric signal and then outputs the electric signal.

The light converting member 24 may be, for example, a light distribution converting member that converts light distribution, and may comprise a lens and a diffusion member. The light converting member 24 is not necessarily a required element, and the endoscope may be configured so that the light guided by the optical fiber 20 is applied to the subject as it is depending on performance required for the endoscope.

In the following explanation, the light output from the light source section 12 is referred to as a light source light, and the light sent out from the scope insertion section 22 is referred to as an illumination light.

The image sensor 26 is not necessarily required to be disposed at the distal end of the scope insertion section 22. An optical member may be disposed at the distal end of the scope insertion section 22, and the image sensor 26 may be disposed in the rear of the scope insertion section 22 or outside the scope insertion section 22. It is also possible to provide a system in which the optical member is disposed in the scope insertion section 22, and not the image sensor 26 but an eyepiece is disposed in the rear of the scope insertion section 22 so that a user optically directly observes a subject image.

The endoscope also comprises an image forming section 32 that forms an image on the basis of an electric signal output from the image sensor 26, and an image display 34 that displays the image formed by the image forming section 32.

[Light Source Section]

It has heretofore been considered that the application of a broad light without any wavelength lack in the whole visible light wavelength range to the subject as an illumination light is essential for a high-quality observation with high image reproducibility. Here, the visible light is a light having a wavelength of 380 nm to 780 nm.

However, it has recently become obvious that even an illumination light that is a combination of multiple single-wavelength lights such as laser lights can be high enough in performance (color rendering properties) as an illumination light (e.g. A. Neumann et at., Opt. Exp., 19, S4, A982 (Jul. 4, 2011)).

Figure 2:
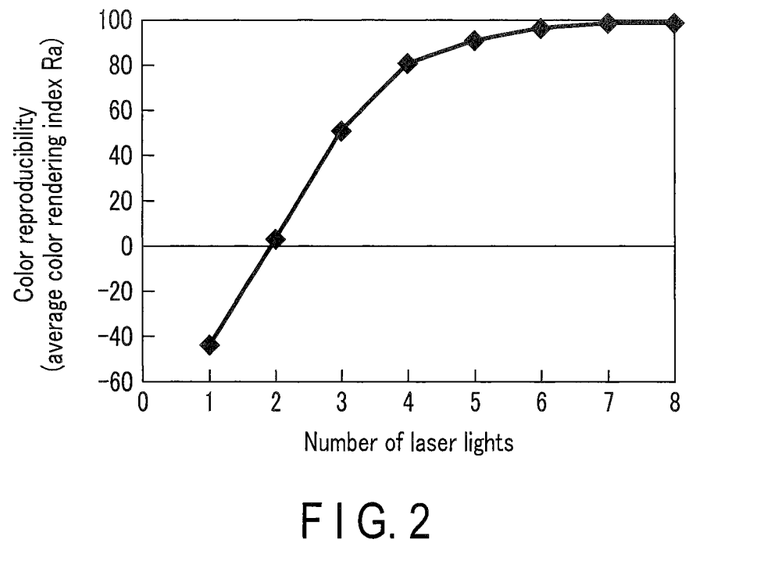
FIG. 2 is a graph showing a relationship between the number of laser lights and the color reproducibility.

The present inventors calculated an average color rendering index Ra that was one of illuminator quality evaluation parameters defined by, for example, JIS for various wavelengths and various numbers of lasers. As a result, as shown in FIG. 2, it was found that performance equal to or more than that of conventionally used general illumination having a broad spectrum could be obtained by an appropriate combination of laser lights of different wavelengths.

Accordingly, it has become expected that a laser that outputs a light higher in light density and parallelism from a much smaller emission region than a gas light source or an LED that has heretofore been used can be used as a normal light observation light source requiring color rendering properties. A laser light is easy to highly efficiently introduce into a small-diameter light guiding component such as an optical fiber and can therefore obtain a specific advantage of being able to obtain a low-power-consumption, high-luminance, and high-color-rendering illumination with a small diameter particularly in an observation apparatus such as an endoscope apparatus for use in observations in closed spaces.

The light source section 12 is a light source configured on the basis of such a background, and comprises multiple lasers 14A, 14B, 14C, 14D, 14E, and 14F that respectively emit lights of wavelengths different from one another, optical fibers 16 optically coupled to the lasers 14A to 14F, respectively, and a combiner 18 that mixes the lights guided by the optical fibers 16.

The lasers 14A to 14F can respectively emit lights such as visible lights having their central wavelengths different from one another. For example, the laser 14A can emit a light having a wavelength of 440 nm, the laser 14B can emit a light having a wavelength of 470 nm, the laser 14C can emit a light having a wavelength of 530 nm, the laser 14D can emit a light having a wavelength of 590 nm, the laser 14E can emit a light having a wavelength of 640 nm, and the laser 14F can emit a light having a wavelength of 680 nm.

[Dyes]

This endoscope is assumed to be used in a "dye observation method". Therefore, a subject in which a predetermined dye is dispersed is assumed as a subject. Here, the predetermined dye is a dye that is assumed to be used in an observation using an endoscope, and in a medical endoscope, the predetermined dye is a dye used to emphasize and observe subject information that is difficult to obtain in the normal light observation. The dye also includes a fluorescent dye. The fluorescent dye is a dye that absorbs a certain wavelength and emits a light having a wavelength different from the former wavelength. The dye is a material having a light absorbing wavelength region and a light transmission wavelength region in a visible light wavelength region. The dispersion not only includes blowing a liquid including the dye against the subject but also includes pouring the liquid into the subject or locally injecting the liquid into the subject.

The main dyes to be dispersed in the subject are known to be indigo carmine, toluidine blue, and crystal violet (pyoktanin).

Indigo carmine is a typical dye in a currently most frequently used contrast method, and is widely used in lesions in the stomach, small intestine, and large intestine from normal examinations to close examinations. Indigo carmine is comparatively harmless to humans and is high in security, and can therefore be safely used for any patient. Indigo carmine does not show any reaction with a living body, but the liquid remains in protrusions and depressions and thereby enables small depressions and protrusions to be observed in an emphasized manner.

Toluidine blue is a dye mostly used in a lesion in the esophagus. When a defect is formed in the esophagus epithelium, toluidine blue dyes a necrotic material adhering thereto in blue and thereby enables the defect part to be observed in an emphasized manner.

Crystal violet (pyoktanin) is a dye to dye cell nuclei, and is mostly used in magnifying endoscopy for the large intestine. Crystal violet (pyoktanin) dyes cell nuclei that constitute a lesion in blue, and thereby enables the lesion part to be observed in an emphasized manner. There has been established diagnostics that observes this form of pattern with a magnifying endoscope and thereby judges the characteristics of the lesion (e.g. whether the lesion is benign or malignant).

[Observation Mode Switch]

The endoscope also comprises an observation mode switch 42 to switch observation modes. Here, the observation modes include a dye valid observation mode allowed to acquire a normal light image in which the dyes dispersed in the subject are visually recognized well, and a dye invalid observation mode allowed to acquire a normal light image in which the dyes dispersed in the subject are substantially not visually recognized. Both the dye valid observation mode and the dye invalid observation mode are modes to observe images showing an appearance of the subject when a white light is applied thereto. The observation mode switch 42 also comprises an interface for the user to select an observation mode.

The light source section 12 can selectively output light source lights in accordance with switching of the observation modes by the observation mode switch 42, and the scope insertion section 22 can selectively emit illumination lights accordingly. That is, the kinds of illumination lights to be applied to the subject from the scope insertion section 22 can be switched by the observation mode switch 42.

The illumination lights include a dye valid illumination light that is sent out when the dye valid observation mode is selected, and a dye invalid illumination light that is sent out when the dye invalid observation mode is selected.

The endoscope also comprises a spectrum controller 44 that changes irradiation spectra of the illumination lights in accordance with switching of the observation modes by the observation mode switch 42 in order to create the dye valid illumination light and the dye invalid illumination light. The spectrum controller 44 can independently control the on/off and output of each of the lasers 14A to 14F.

The endoscope also comprises an image forming method storage for each observation mode 46 that feeds information regarding an image forming method suited to each observation mode into the image forming section 32. The image forming section 32 acquires, from the observation mode switch 42, information regarding the observation mode selected by the observation mode switch 42, acquires a corresponding image forming method from the image forming method storage for each observation mode 46, and then forms an image suited to the selected observation mode.

The endoscope also has a control condition storage 48 that feeds control condition information into the spectrum controller 44 to create the illumination lights. The spectrum controller 44 controls each of the lasers 14A to 14F on the basis of the control condition information fed from the control condition storage 48. The control condition information may be, for example, information indicating a combination of the lasers 14A to 14F that are turned on and off in order to create the dye valid illumination light and the dye invalid illumination light, and preferably, may further have information indicating the outputs of the lasers 14A to 14F such that the brightness of the images obtained in the dye valid observation mode and the dye invalid observation mode may be substantially the same to reduce an unusual feeling that the user may have when the observation modes are switched.

[Dye Valid Illumination Light and Dye Invalid Illumination Light]

The dye valid illumination light includes a light of a wavelength out of the main absorbing wavelength region of the dye dispersed in the subject, and a light of a wavelength in the main absorbing wavelength region of the dye dispersed in the subject.

The dye invalid illumination light includes a light of the wavelength out of the main absorbing wavelength region of the dye dispersed in the subject, but does not include a light of the wavelength in the main absorbing wavelength region of the dye dispersed in the subject.

Here, the "main absorbing wavelength region" is a wavelength region range indicating an absorptance higher than ½ of an absorptance at a wavelength showing the highest absorptance among visible lights in an absorption spectrum of the dye. A light having a wavelength that is absorbed at an absorptance that is less than or equal to ½ of the absorptance of an absorption peak wavelength can ensure the transparency of the dye by applying an adequate quantity of light.

The main absorbing wavelength region is preferably a wavelength region range indicating an absorptance higher than ¹⁄₁₀ of an absorptance at the absorption peak wavelength. A light having a wavelength that is absorbed at an absorptance that is less than or equal to ¹⁄₁₀ of the absorptance at the absorption peak wavelength can ensure sufficient transparency of the dye regardless of the quantity of light.

"Including a light" means that the intensity of the light is higher than or equal to ½ of the light having the highest intensity among the lights having various wavelengths included in the illumination light.

"Not including a light" means that the intensity of the light is less than or equal to ¹⁄₁₀ of the light having the highest intensity among the lights having various wavelengths included in the illumination light.

The presence of a light that has the wavelength in the main absorbing wavelength region of the dye dispersed in the subject and that has intensity higher than or equal to ½ of the light having the highest intensity included in the illumination light greatly influences the optical function of the dye. That is, if such a light is included in the illumination light, the optical characteristics of the dye validly act, and an image to be obtained allows the dye to be visually recognized well. In contrast, if such a light is not included in the illumination light, the optical characteristics of the dye are substantially invalidated, and the dye substantially behaves as a transparent liquid, and an image to be obtained does not substantially allow the dye to be visually recognized.

The presence of a light that has the wavelength in the main absorbing wavelength region of the dye dispersed in the subject and that has intensity less than or equal to ¹⁄₁₀ of the light having the highest intensity included in the illumination light hardly influences the optical function of the dye. That is, even if such a light is included in the illumination light, the light hardly propagates to the image sensor 26 and does not make any difference.

The dye invalid illumination light preferably includes both a light having a short-wavelength-side wavelength and a light having a long-wavelength-side wavelength for the main absorbing wavelength region of the dye dispersed in the subject. For example, in the case of the dye invalid illumination light for the dye that mainly absorbs red, red component information for the subject will lack if all spectral components of a red region are only removed. This also applies to the dye that mainly absorbs blue. To avoid major lack of subject information in the vicinity of a dye absorbing region, it is preferable that the dye invalid illumination light have lights on both sides of a dye absorbing wavelength region, and a light in a violet region or a deep red region of around 700 nm be used as an alternative light for the light in the dye absorbing wavelength region to obtain information regarding a blue region or a red region.

[Typical Dyes and Dye Valid Illumination Light and Dye Invalid Illumination Light]

Figure 3:
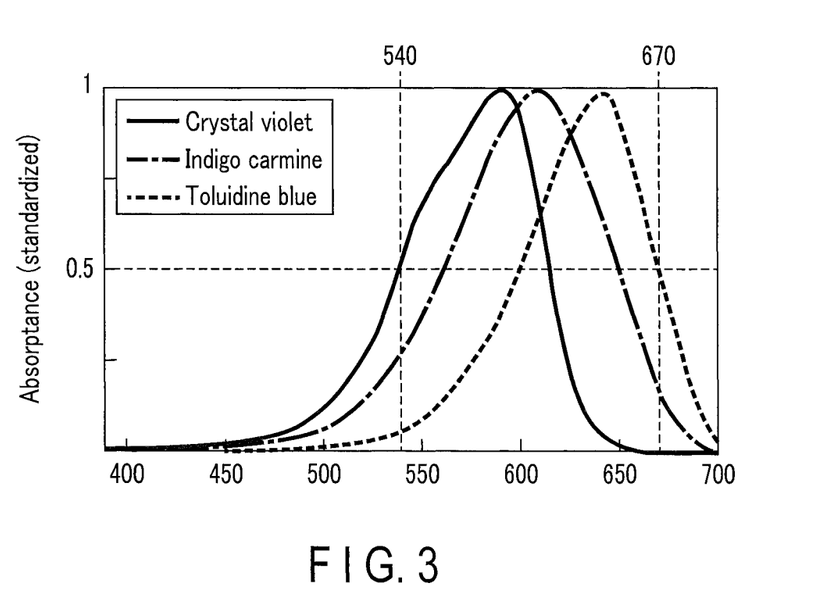
FIG. 3 shows absorption spectra of indigo carmine, toluidine blue, and crystal violet (pyoktanin)

Absorption spectra of indigo carmine, toluidine blue, and crystal violet (pyoktanin) are shown in FIG. 3. Indigo carmine, toluidine blue, and crystal violet (pyoktanin) are typical dyes that are frequently used in the dye observation method. As obvious from FIG. 3, a light having a wavelength of less than 540 nm and a light having a wavelength of 670 nm or more are less than or equal to ½ regarding the absorptance for any one of indigo carmine, toluidine blue, and crystal violet (pyoktanin). The dye to be dispersed in the subject may be any one of indigo carmine, toluidine blue, and crystal violet (pyoktanin). In this case, the dye valid illumination light desirably includes a visible light having a wavelength of less than 540 nm, and a light having a wavelength of 540 nm or more and less than 670 nm. The dye invalid illumination light includes a visible light having a wavelength of less than 540 nm, and does not include a light having a wavelength of 540 nm or more and less than 670 nm, but desirably includes a visible light having a wavelength of 670 nm or more instead. The above dye valid illumination light and dye invalid illumination light are also valid in the dye observation method for the subject in which any one of indigo carmine, toluidine blue, and crystal violet (pyoktanin) is dispersed.

Figure 4:
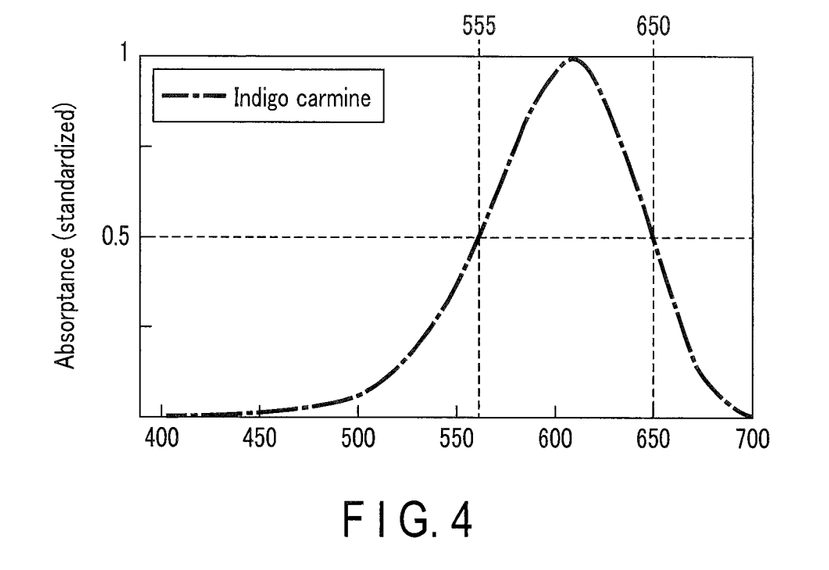
FIG. 4 shows an absorption spectrum of indigo carmine.

The absorption spectrum of indigo carmine is shown in FIG. 3. As obvious from FIG. 4, a light having a wavelength of less than 555 nm and a light having a wavelength of 670 nm or more are less than or equal to ½ regarding the absorptance for indigo carmine. The dye to be dispersed in the subject may be indigo carmine. In this case, the dye valid illumination light desirably includes a visible light having a wavelength of less than 555 nm, and a light having a wavelength of 555 nm or more and less than 650 nm. The dye invalid illumination light includes a visible light having a wavelength of less than 555 nm, and does not include a light having a wavelength of 555 nm or more and less than 650 nm, but desirably includes a visible light having a wavelength of 650 nm or more instead. The above dye valid illumination light and dye invalid illumination light are valid in the dye observation method for the subject in which indigo carmine is dispersed.

[Narrow-band Light]

The dye valid illumination light and the dye invalid illumination light preferably comprise lights that are combinations of multiple narrow-band lights. The narrow-band light is a light in which the full width at half maximum (FWHM) of an emission spectrum of a light sent out from a light source is less than 50 nm. The dye invalid illumination light desirably includes one or more visible-light narrow-band lights on each of both the long-wavelength side and short-wavelength side of the main absorbing wavelength region of the dye. Moreover, each of the wavelengths of the narrow-band lights on the long-wavelength side and short-wavelength side closest to the main absorbing region of the dye is desirably as close to the main absorbing region of the dye as possible. This allows the optical function inherent in the dye to be reduced and the subject information in the vicinity of the dye absorbing region to be acquired, so that an unusual feeling regarding the appearance of the subject at the time of the dye invalid observation can be reduced. For example, in the normal light observation, when color imaging is performed in general, subject information of three kinds (three colors) is acquired every 100 nm, for example, at 400 s nm in a blue region and at 500 s nm a green region sometimes with slight overlaps, whereby faithful color reproduction is achieved. Faithful color reproduction can not be achieved without any one of the three colors, so that the wavelengths of the lights that constitute the illumination light are preferably always present in the respective wavelength regions of the three colors. When each color has 100 nm width, a narrow-band light having a full width at half maximum (FWHM) smaller than 50 nm that is half 100 nm is preferable if faithful color reproduction is to be obtained to avoid the absorbing wavelength of the dye. As a result, the narrow-band light having a wavelength close to the absorbing wavelength region of the dye can be included in the illumination light, and the subject information in the vicinity of the dye absorbing wavelength region can be faithfully acquired through the dye. A laser, which has the smallest full width at half maximum (FWHM), is preferable as a light source, and the laser permits the narrow-band light having a wavelength close to the dye absorbing wavelength to be easily included in the illumination light. An LED or an OLED that emits a narrow-band light having a full width at half maximum (FWHM) of 50 nm or less, or a phosphor that is excited by a light source is also one of preferable light sources.

[Operation]

The laser lights (narrow-band lights) emitted from one or more lasers 14A to 14F in the light source section 12 are guided by the optical fibers 16, and mixed into a light source light by the combiner 18. The light source light is guided to the light converting member 24 at the distal end of the scope insertion section 22 by the optical fiber 20, and changed into an illumination light suited to illumination by the light converting member 24. The illumination light is sent out forward from the distal end of the scope insertion section 22.

The image sensor 26 provided at the distal end of the scope insertion section 22 acquires an optical image of the subject illuminated by the illumination light, and converts the optical image into an electric signal and then feeds the electric signal into the image forming section 32. The image forming section 32 converts the fed electric signal into a signal suited to display, and sends the signal to the image display 34. The image display 34 displays an image in accordance with the received signal.

When the dye valid observation mode is selected by the user, the dye valid observation mode is selected in the observation mode switch 42, and the relevant information is transmitted to the spectrum controller 44. Accordingly, the spectrum controller 44 acquires, from the control condition storage 48, information regarding the combination of the lasers 14A to 14F that are turned on and off in order to create a dye valid observation light, and information regarding the outputs of the lasers 14A to 14F that are turned on, and then controls the on/off and outputs of the lasers 14A to 14F in accordance with the control condition information.

For example, in order to create the dye valid illumination light, the laser 14A having an emission wavelength of 440 nm, the laser 14B having an emission wavelength of 470 nm, the laser 14C having an emission wavelength of 530 nm, the laser 14D having an emission wavelength of 580 nm, and the laser 14E having an emission wavelength of 640 nm are turned on.

The light that is a mixture of the lights having the above emission wavelengths functions as a normal illumination light. As a result, a high-performance illumination light is applied to the subject, a faithful subject reflection image appears, and the image is received by the image sensor 26.

The image forming section 32 processes the electric signal received from the image sensor 26 in accordance with the image forming method suited to the dye valid observation mode, thereby forming an image. To this end, the image forming section 32 previously acquires, from the observation mode switch 42, information indicating that the dye valid observation mode is selected, and refers to the image forming method storage for each observation mode 46 for the image forming method suited to the dye valid observation mode to form an image.

In contrast, when the dye invalid observation mode is selected by the user, the on/off and outputs of the lasers 14A to 14F are controlled by the spectrum controller 44 in accordance with the control condition information to create the dye invalid illumination light through a process similar to the above.

For example, to create the dye invalid illumination light, the laser 14A having an emission wavelength of 440 nm, the laser 14B having an emission wavelength of 470 nm, the laser 14C having an emission wavelength of 530 nm, and the laser 14F having an emission wavelength of 680 nm are turned on.

The illumination light that is a mixture of the lights having the above emission wavelengths also functions as a normal illumination light in a manner similar to the previously described dye valid illumination light.

The image forming section 32 processes the electric signal received from the image sensor 26 in accordance with the image forming method suited to the dye valid observation mode, thereby forming an image.

Figure 5:
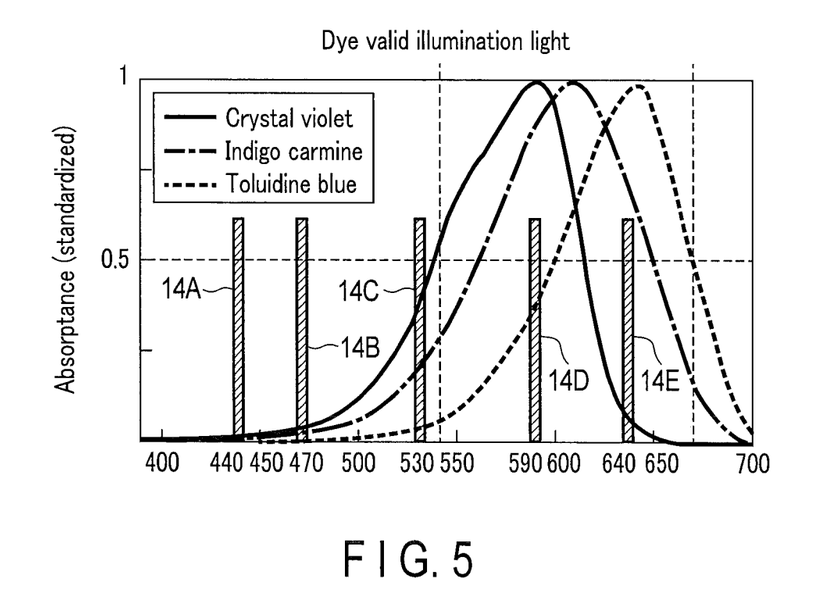
FIG. 5 shows each spectrum of the narrow-band light included in the dye valid illumination light in the endoscope shown in FIG. 1, over the absorption spectra of indigo carmine, toluidine blue, and crystal violet (pyoktanin)
Figure 6:
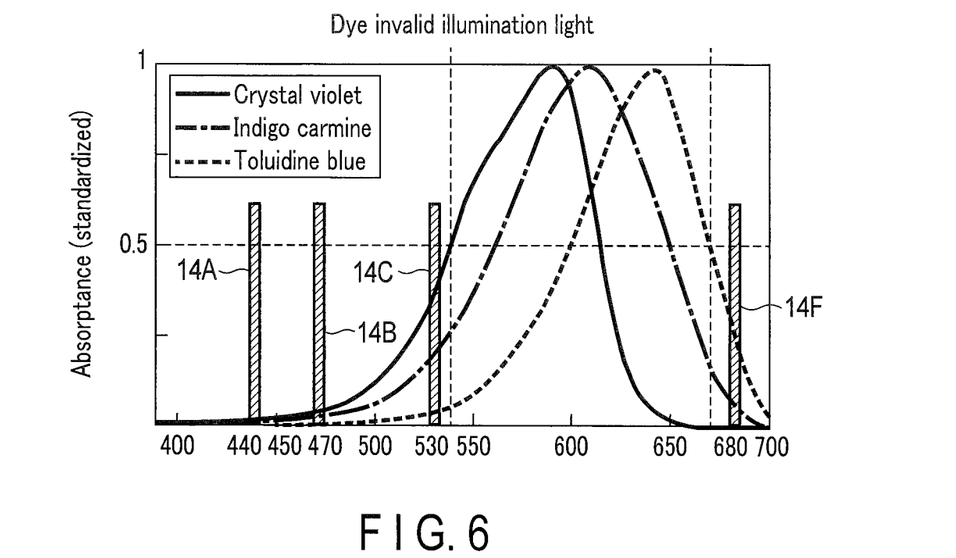
FIG. 6 shows each spectrum of the narrow-band light included in the dye invalid illumination light in the endoscope shown in FIG. 1, over the absorption spectra of indigo carmine, toluidine blue, and crystal violet (pyoktanin)

Each spectrum of the narrow-band light included in the dye valid illumination light is shown over the absorption spectra of indigo carmine, toluidine blue, and crystal violet (pyoktanin) in FIG. 5. Each spectrum of the narrow-band light included in the dye invalid illumination light is shown over the absorption spectra of indigo carmine, toluidine blue, and crystal violet (pyoktanin) in FIG. 6.

For example, if the dye valid illumination light is applied to the subject in which an indigo carmine aqueous solution is dispersed, the light having a wavelength of 590 nm and the light having a wavelength of 640 nm are strongly absorbed by the indigo carmine dye, and the light having a wavelength of 440 nm, the light having a wavelength of 470 nm, and the light having a wavelength of 530 nm are mostly reflected by the indigo carmine dye. Thus, the depressions that retain indigo carmine only appear blue, so that a satisfactory dye valid observation is possible.

In contrast, if the dye invalid illumination light is applied to the subject in which the indigo carmine aqueous solution is dispersed, since the dye invalid illumination light does not include the light having the wavelength in the absorbing wavelength region of the indigo carmine dye and since indigo carmine does not have light scattering characteristics and reflection characteristics in the absorbing wavelength region, the presence of the dye is substantially not imaged. Thus, under the dye invalid illumination light, indigo carmine behaves equivalently to a "transparent liquid", and the living body color of the subject underneath is faithfully imaged.

Figure 7:
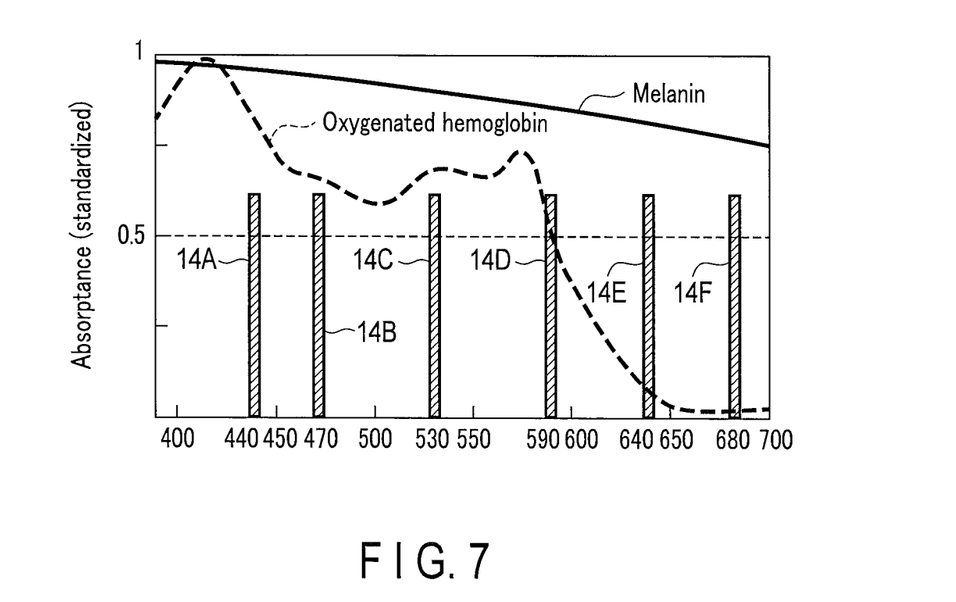
FIG. 7 shows spectra of blood and melanin, which are the main components of living bodies, over the emission wavelengths of the lasers.

FIG. 7 shows the spectra of blood and melanin, which are the main components of living bodies, over the emission wavelengths of the lasers 14A to 14F. As obvious from FIG. 7, if the purpose is limited to the imaging of the inside of the living body, hemoglobin and melanin are absorbed at substantially the same intensity in the vicinity of 640 nm and in the vicinity of 680 nm, so that alternatively using the lights having these wavelengths hardly affects a living body image to be obtained.

Furthermore, the electric signal output from the image sensor 26 is processed in the image forming section 32 in accordance with the image forming method suited to the observation mode. For example, the electric signal output from the image sensor 26 in the dye invalid observation mode is processed so that color information corresponding to the light having a wavelength of 580 nm and the light having a wavelength of 640 nm that are not included in the dye invalid illumination light may be compensated for on the basis of the light having a wavelength of 530 nm and the light having a wavelength of 680 nm. Consequently, an image that achieves an appearance of the subject when a white light is applied thereto is obtained in both the dye valid observation mode and the dye invalid observation mode.

Figure 8:
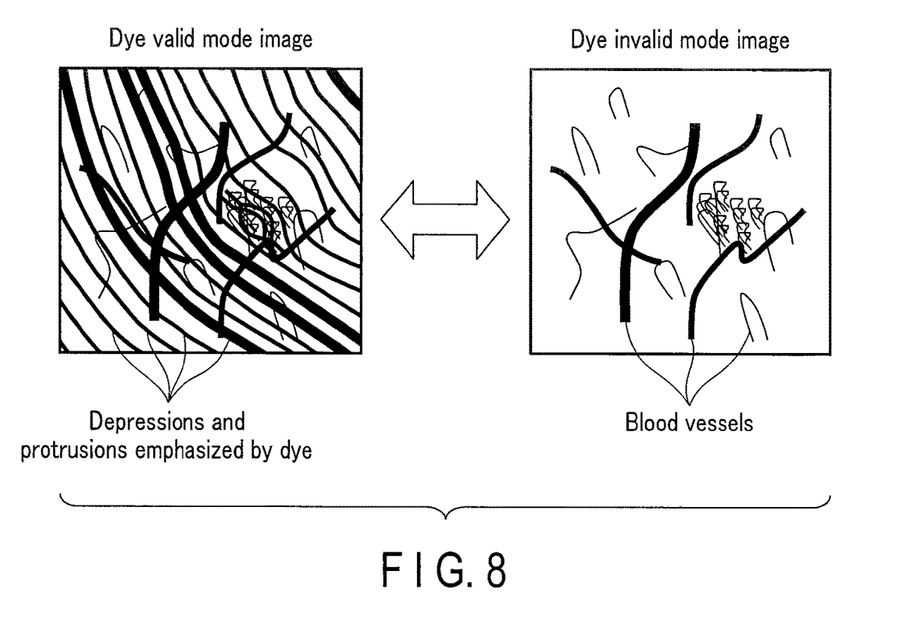
FIG. 8 shows two kinds of observation images, a dye valid observation image and a dye invalid observation image, obtained by using the endoscope shown in FIG. 1.

Two kinds of observation images shown in FIG. 8 are obtained by using the endoscope to switch the dye valid observation mode and the dye invalid observation mode.

[Modifications]

The illumination light as the normal light observation is not limited to the "white light". The illumination light to obtain an appearance of the subject when a white light is applied thereto does not need to be the white light. Especially in an observation apparatus such as an endoscope under an environment that hardly allows external light to come in, it is relatively easy to image under an illumination light that is not white, and reproduce and process the relevant information into an appearance when illuminated by the white light.

The observation to which switching of the dye valid observation and the dye invalid observation are applied is not limited to the normal light observation. The dye valid observation and the dye invalid observation may be switched in the kind of observation in which lights having certain wavelengths in one or more colors are applied to emphasize and display blood vessels and cells in a part of the subject, a certain material such as a fluorescent material, components, and shapes.

The light source to be applied to the light source section 12 is not limited to a solid-state light source such as a laser or an LED. A gas light source such as xenon and halogen may be used. These light sources generally have emission spectra over the whole visible light range. In this case, a cut filter that cuts the light in the absorbing wavelength region of the dye has only to be disposed in front of the aforementioned light source to have an emission spectrum corresponding to the dye invalid illumination light that does not include the light having the wavelength in the absorbing wavelength region of the dye.

Figure 9:
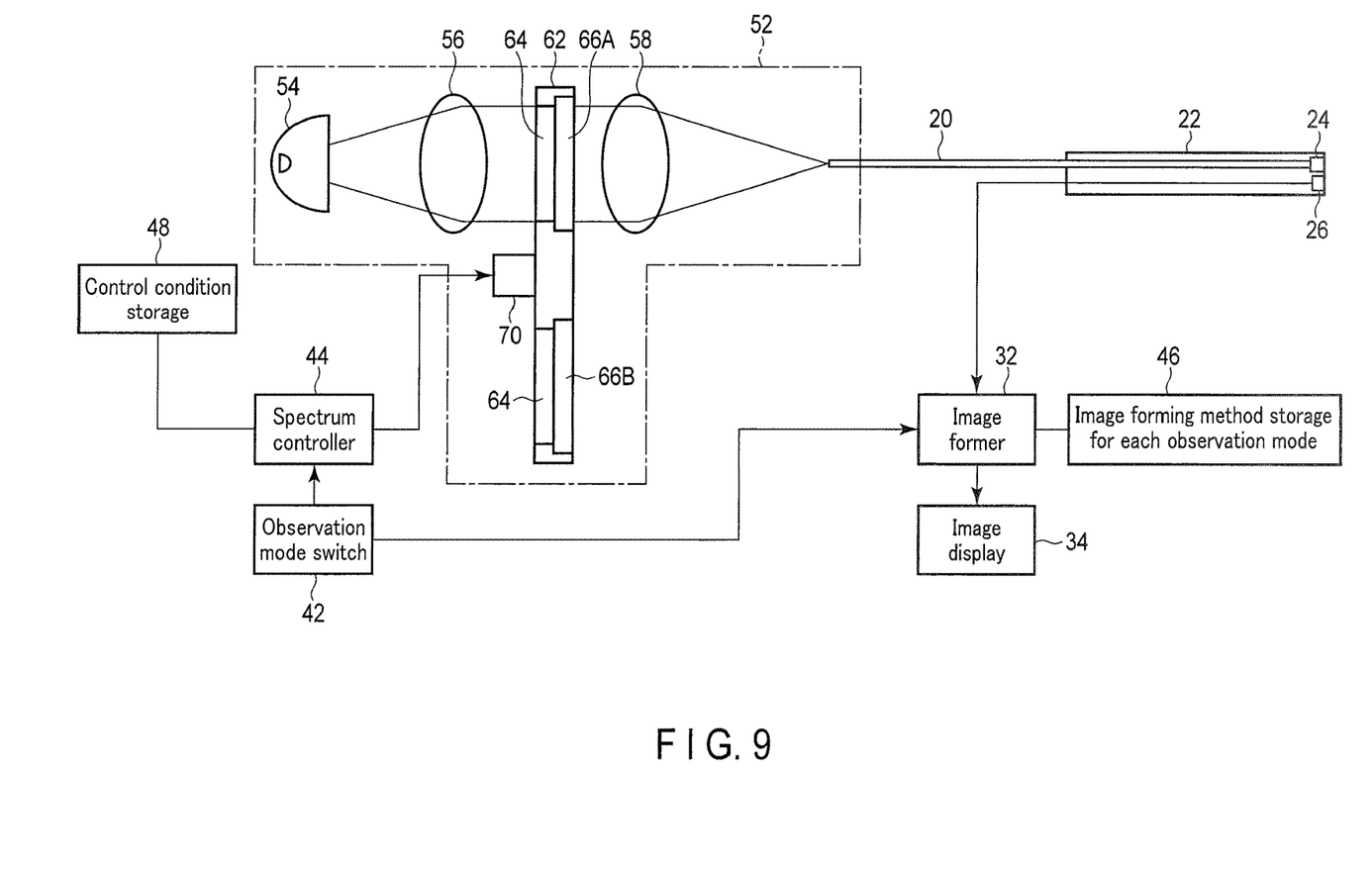
FIG. 9 shows a schematic constitution of an endoscope according to a constitution using a gas light source.
Figure 10:
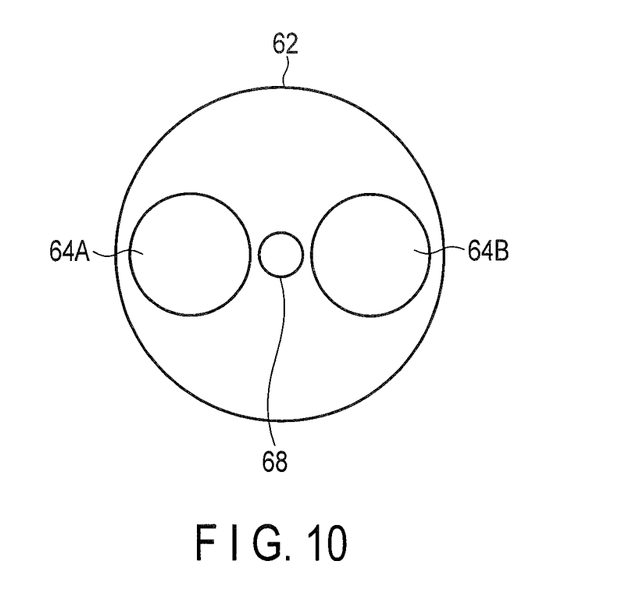
FIG. 10 is a plan view of a turret shown in FIG. 9.

A schematic constitution of the endoscope according to such a constitution is shown in FIG. 9. In FIG. 9, components having the same reference marks as those of the components shown in FIG. 1 are similar components, and are not described in detail. FIG. 10 is a plan view of a turret shown in FIG. 9.

In this endoscope, a light source section 52 includes a light source 54 having emission spectra over the whole visible light range, a lens 56 that changes a light emitted from the light source 54 into a substantially parallel beam, a lens 58 that converts the parallel beam into a convergent light and then couples the convergent light to the optical fiber 20, and a turret 62 disposed between the lens 56 and the lens 58. The turret 62 is supported to be rotatable around a rotational axis 68 by a motor 70. The turret 62 has multiple, for example, two light transmission windows 64 that can be selectively disposed on an optical path of the lens 56 and the lens 58. The two light transmission windows 64 are respectively provided with an optical filter 66A suited to create the dye valid illumination light, and an optical filter 66B suited to create the dye invalid illumination light.

The optical filter 66A may be transparent over the whole visible light range, and may comprise, for example, a mere transparent plate or aperture. The optical filter 66B may comprise, for example, a band cut filter or a color filter that cuts off a light having a wavelength of 540 nm or more and less than 670 nm.

The spectrum controller 44 controls the motor 70 in accordance with the observation mode selected by the observation mode switch 42, that is, in accordance with whether the dye valid observation mode or the dye invalid observation mode is selected, and selectively disposes the optical filter 66A or 66B suited to the observation mode on the optical path of the lens 58.

Figure 11:
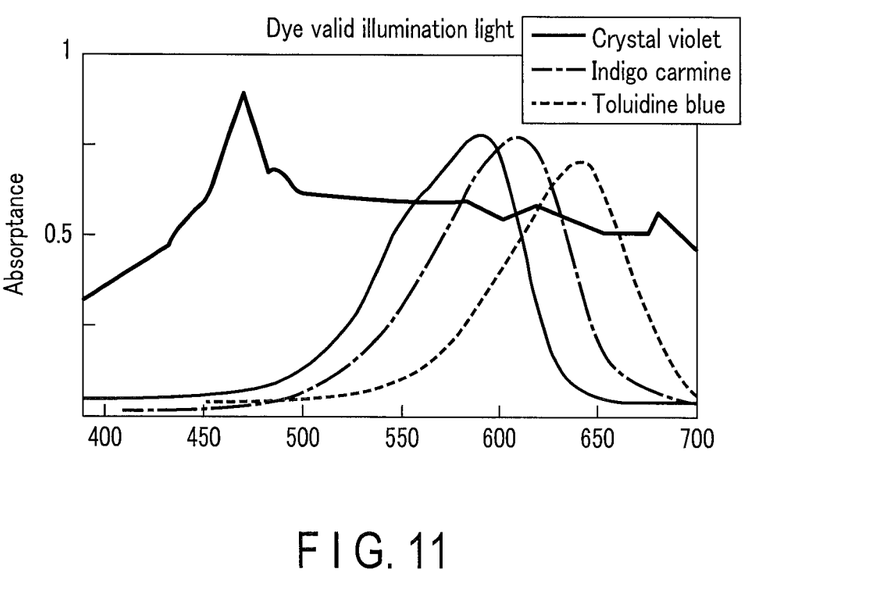
FIG. 11 shows a spectrum of the dye valid illumination light in the endoscope shown in FIG. 9, over the absorption spectra of indigo carmine, toluidine blue, and crystal violet (pyoktanin)
Figure 12:
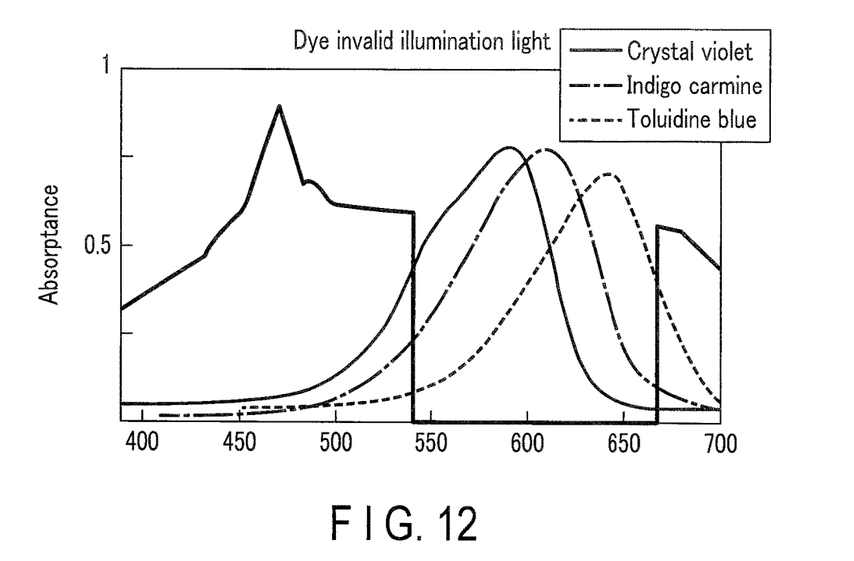
FIG. 12 shows a spectrum of the dye invalid illumination light in the endoscope shown in FIG. 9, over the absorption spectra of indigo carmine, toluidine blue, and crystal violet (pyoktanin)

A spectrum of the dye valid illumination light is shown over the absorption spectra of indigo carmine, toluidine blue, and crystal violet (pyoktanin) in FIG. 11. A spectrum of the dye invalid illumination light is shown over the absorption spectra of indigo carmine, toluidine blue, and crystal violet (pyoktanin) in FIG. 12.

[Advantageous Effects]

Color reproducibility in a living body is high when the dye valid illumination light is used in an observation.

When an observation is conducted with the dye valid illumination light after a dye is dispersed, the dye can be correctly captured, and a satisfactory dye observation can be conducted.

If the illumination light is switched to the dye invalid illumination light to conduct an observation after a dye is dispersed, a surface structure inherent in a living body that is not affected by the dye can be imaged.

Since the control condition storage 48 is provided, it is possible to achieve illumination switching that conforms to the observation mode switched by the observation mode switch 42 and gives no unusual feeling of brightness and color during the observation mode switching.

Since narrow-band lights are combined into an illumination light, the light having the wavelength that is considerably close to the absorbing wavelength region of the dye can be included in the illumination light, and the dye can be invalidated in the normal light observation without an unusual feeling of the observation image.

Since the dye invalid illumination light includes the narrow-band lights on both the short-wavelength side and long-wavelength side of the main absorbing region of the dye, color information can be acquired substantially over the whole range of the visible lights.

[Second Embodiment]

The present embodiment shows an endoscope having a "simultaneous observation mode" in which a dye valid observation mode image and a dye invalid observation mode image can be visually recognized at the same time.

The apparatus constitution of the endoscope is similar to that shown in FIG. 1.

If the simultaneous observation mode is selected by the user, the observation mode switch 42 alternately switches the observation mode to the dye valid observation mode and the dye invalid observation mode. The switching period is set in accordance with the imaging period of the image sensor 26. For example, the switching period is adjusted to one frame of imaging by the image sensor 26. When the image sensor 26 performs imaging at a period of 30 Hz, the combination of the lasers 14A to 14F that are turned on in order to create the dye valid illumination light and the dye invalid illumination light is switched at a period of 30 Hz.

The image forming section 32 performs image formation by switching and applying the image forming method suited to the dye valid observation mode and the image forming method suited to the dye invalid observation mode at a period of 30 Hz for a received signal fed from the image sensor 26. That is, the image forming section 32 alternately forms the dye valid observation mode image and the dye invalid observation mode image at a period of 30 Hz, and sends information on these images to the image display 34. The image display 34 displays the dye valid observation mode image and the dye invalid observation mode image at the same time, for example, side by side in accordance with the received image information.

Figure 13:
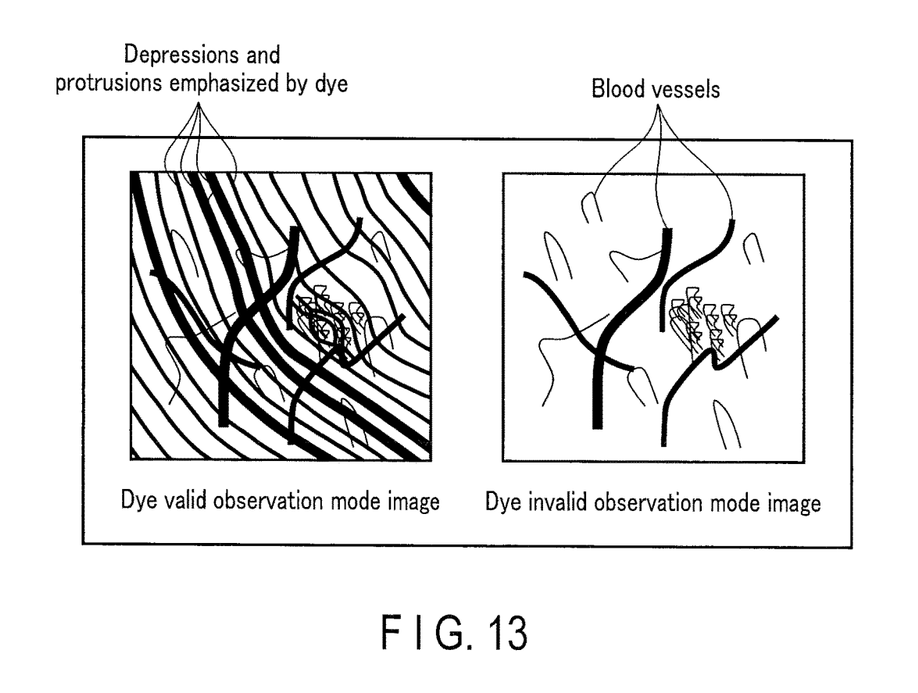
FIG. 13 shows examples of the dye valid observation mode image and the dye invalid observation mode image simultaneously displayed by the image display.

Examples of the dye valid observation mode image and the dye invalid observation mode image simultaneously displayed by the image display 34 are shown in FIG. 13.

The dye valid observation mode image and the dye invalid observation mode image do not necessarily need to be displayed side by side. It is also possible to display the images by image processing that superimposes or overlays the images so that the user can easily recognize the images.

[Advantageous Effects]

Since the dye valid observation mode and the dye invalid observation mode can be substantially simultaneously provided by alternately switching two kinds of illumination lights, the dye valid observation mode image and the dye invalid observation mode image are simultaneously obtained.

Since the laser lights are used as the light sources, the light sources can be instantaneously switched, there are no display troubles such as delays or instability of brightness, and the dye valid observation mode image and the dye invalid observation mode image can be simultaneously displayed in a satisfactory manner.

While certain embodiments of the present invention have been described with reference to the drawings, the present invention is not limited to them and may be modified or altered without departing from the spirit of the invention. The modification or alteration mentioned herein includes proper combinations of the aforesaid embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope for observing a subject in which a dye is dispersed, the dye being a material having a light absorbing wavelength region and a light transmission wavelength region in a visible light wavelength region, the endoscope comprising:

a controller comprising hardware, the controller being configured to switch observation modes, the observation modes including a dye valid observation mode for acquiring an image in which the dye is visually recognized, and a dye invalid observation mode for acquiring an image in which the dye is substantially not visually recognized;

wherein the controller selectively emits illumination lights in accordance with switching of the observation modes by the observation mode switch;

the illumination lights include a dye valid illumination light that is sent out when the dye valid observation mode is selected, and a dye invalid illumination light that is sent out when the dye invalid observation mode is selected, the dye valid illumination light includes a visible light of a wavelength out of the main absorbing wavelength region of the dye, and a light of a wavelength in the main absorbing wavelength region of the dye, and the dye invalid illumination light includes a visible light of the wavelength out of the main absorbing wavelength region of the dye, but does not include a light of the wavelength in the main absorbing wavelength region of the dye.

2. The endoscope according to claim 1, wherein the controller is configured to change irradiation spectra of the illumination lights in accordance with switching of the observation modes in order to create the dye valid illumination light and the dye invalid illumination light.

3. The endoscope according to claim 2, further comprising a light source, and a spectrum changer that suitably changes a spectrum of a light emitted from the light source, the spectrum changer comprising light transmission windows selectively disposed on an optical path of the light emitted from the light source, and an optical filter that changes the spectrum of the light emitted from the light source provided in at least one of the light transmission windows, wherein the controller is configured to control the position of the light transmission window disposed on the optical path of the light emitted from the light source.

4. The endoscope according to claim 2, further comprising multiple light sources that respectively emit lights, wherein the controller is configured to control the on/off and outputs of the multiple light sources.

5. The endoscope according to claim 3, further comprising a storage device for feeding control condition information into the spectrum controller to create the illumination lights, wherein the controller is configured to control on the basis of the control condition information fed from the storage device.

6. The endoscope according to claim 5, wherein the dye valid observation mode and the dye invalid observation mode are modes to observe a normal light image that achieves an appearance of the subject when a white light is applied to the subject.

7. The endoscope according to claim 6, wherein each of the illumination lights comprises a light in which multiple narrow-band lights are combined, and each of the narrow-band lights is a light in which the full width at half maximum (FWHM) of an emission spectrum of a light sent out from a light source is less than 50 nm.

8. The endoscope according to claim 7, wherein the dye invalid illumination light includes one or more visible-light narrow-band lights on each of both the long-wavelength side and short-wavelength side of the main absorbing wavelength region of the dye.

9. An endoscope system comprising:
the endoscope according to claim 8,
and the dye, wherein the dye comprises one of indigo carmine, toluidine blue, and crystal violet,
the dye valid illumination light includes a visible light having a wavelength of less than 540 nm, and a light having a wavelength of 540 nm or more and less than 670 nm, and
the dye invalid illumination light does not include a light having a wavelength of 540 nm or more and less than 670 nm, and includes a visible light having a wavelength component of less than 540 nm, and a visible light having a wavelength component of 670 nm or more.

10. An endoscope system comprising:
the endoscope according to claim 8,
and the dye, wherein the dye comprises indigo carmine,
the dye valid illumination light includes a visible light having a wavelength of less than 555 nm, and a light having a wavelength of 555 nm or more and less than 650 nm, and
the dye invalid illumination light does not include a light having a wavelength of 555 nm or more and less than 650 nm, and includes a visible light having a wavelength of less than 555 nm, and a visible light having a wavelength of 650 nm or more.

* * * * *